(12) United States Patent
Mei et al.

(10) Patent No.: US 9,926,259 B1
(45) Date of Patent: Mar. 27, 2018

(54) CATALYST FOR FIXED BED ANILINE RECTIFICATION RESIDUE RECYCLING AND PREPARATION METHOD

(71) Applicant: Wanhua Chemical Group Co., Ltd., Yantai, Shandong (CN)

(72) Inventors: Hua Mei, Shandong (CN); Hao Chen, Shandong (CN); Dewei Yu, Shandong (CN); Congying Zhang, Shandong (CN); Hui Wang, Shandong (CN); Yuan Li, Shandong (CN); Zhongying Chen, Shandong (CN); Zilin Ni, Shandong (CN); Qingmei Jiang, Shandong (CN); Shanjian Cao, Shandong (CN); Zaigang Yang, Shandong (CN); Jun Qu, Shandong (CN); Jinhong Song, Shandong (CN); Bingbo Hu, Shandong (CN)

(73) Assignee: Wanhua Chemical Group Co., Ltd. (CN)

( * ) Notice: Subject to any disclaimer, the term of this patent is extended or adjusted under 35 U.S.C. 154(b) by 0 days.

(21) Appl. No.: 15/720,103

(22) Filed: Sep. 29, 2017

Related U.S. Application Data

(62) Division of application No. 14/913,853, filed as application No. PCT/CN2014/073063 on Mar. 7, 2014.

(30) Foreign Application Priority Data

Sep. 3, 2013 (CN) .......................... 2013 1 0396100

(51) Int. Cl.
| | |
|---|---|
| *C07C 209/62* | (2006.01) |
| *B01J 37/03* | (2006.01) |
| *B01J 23/83* | (2006.01) |
| *C07C 209/72* | (2006.01) |
| *B01J 23/00* | (2006.01) |
| *B01J 23/86* | (2006.01) |
| *B01J 23/887* | (2006.01) |
| *B01J 37/08* | (2006.01) |
| *B01J 37/02* | (2006.01) |
| *B01J 23/75* | (2006.01) |
| *C07C 211/35* | (2006.01) |

(52) U.S. Cl.
CPC .......... *C07C 209/62* (2013.01); *B01J 23/002* (2013.01); *B01J 23/75* (2013.01); *B01J 23/83* (2013.01); *B01J 23/866* (2013.01); *B01J 23/8871* (2013.01); *B01J 37/0236* (2013.01); *B01J 37/03* (2013.01); *B01J 37/031* (2013.01); *B01J 37/035* (2013.01); *B01J 37/08* (2013.01); *C07C 209/72* (2013.01); *C07C 211/35* (2013.01); *B01J 2523/36* (2013.01); *B01J 2523/3706* (2013.01); *B01J 2523/3712* (2013.01); *B01J 2523/41* (2013.01); *B01J 2523/48* (2013.01); *B01J 2523/67* (2013.01); *B01J 2523/68* (2013.01); *B01J 2523/845* (2013.01); *B01J 2523/847* (2013.01); *C07C 2601/14* (2017.05)

(58) Field of Classification Search
None
See application file for complete search history.

(56) References Cited

U.S. PATENT DOCUMENTS 6,350,923 B1 * 2/2002 Eller .................... C07C 29/141
568/853

* cited by examiner

*Primary Examiner* — Sudhakar Katakam
*Assistant Examiner* — Jennifer C Sawyer
(74) *Attorney, Agent, or Firm* — Kramer Levin Naftalis & Frankel LLP

(57) ABSTRACT

The present invention relates to a catalyst for fixed bed aniline rectification residue recycling and preparation method thereof. Based on the total weight of the catalyst, the catalyst comprises the following components in percentage by weight: 5-40% of an active component, 2-30% of a first cocatalyst component, 10-30% of a second cocatalyst component and the balance of carrier, wherein the active component is NiO; the first cocatalyst component is one or more of Fe, Mo, Cr or Co oxide; and the second cocatalyst component is one or more of La, Zr, Y or Ce oxide. The catalyst is prepared through co-precipitation. The catalyst shows high activity and stability in the waste liquid treatment process, and can still maintain high rectification residue cracking rate after reaction of 200 hours.

6 Claims, 1 Drawing Sheet

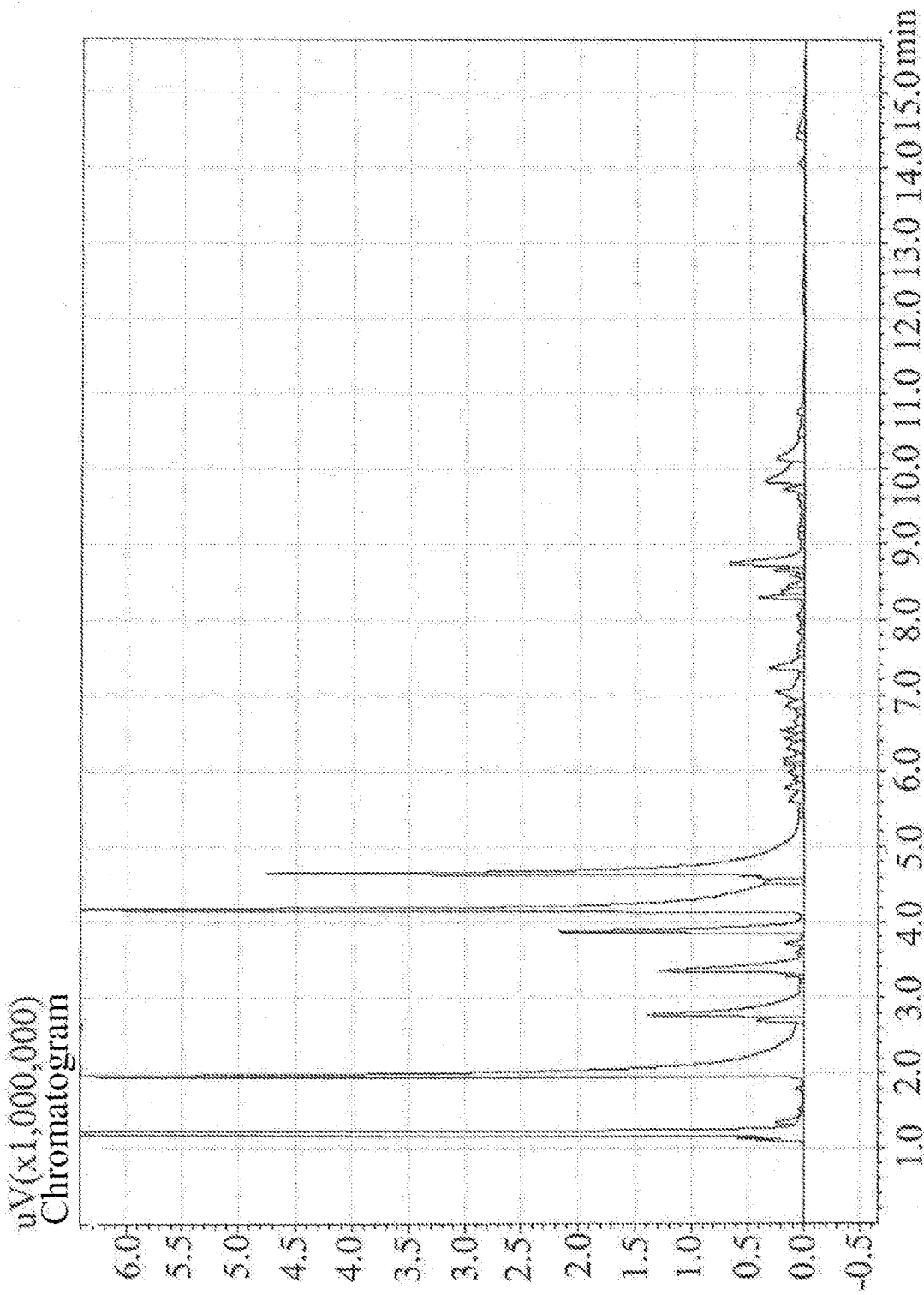

CATALYST FOR FIXED BED ANILINE RECTIFICATION RESIDUE RECYCLING AND PREPARATION METHOD

RELATED APPLICATIONS

This application is a divisional and claims the benefit of priority under 35 U.S.C. § 120 of U.S. application Ser. No. 14/913,853, filed on Feb. 23, 2016, which is a National Stage Entry under 35 U.S.C. § 371 of International Patent Application No. PCT/CN14/73063, filed on Mar. 7, 2014, which claims the benefit of priority of Chinese Patent Application No. 201310396100.6, filed on Sep. 3, 2013.

FIELD OF THE INVENTION

The present invention relates to the use of a catalyst for fixed bed aniline rectification residue recycling.

BACKGROUND OF THE INVENTION

Aniline is a colorless, oily liquid with a strong odor and toxicity. It is an important chemical intermediate, and thus is widely used for producing rubber processing aids, dyes, photographic chemicals, pharmaceuticals, pesticides, explosives, polyurethanes and the like. The production methods of aniline comprise phenol ammoniation, iron powder reduction and catalytic hydrogenation of nitrobenzene.

Taking into account the source of raw materials, energy consumption, environmental protection and so on, most manufacturers use catalytic hydrogenation of nitrobenzene. The catalytic hydrogenation may be divided into two processes, i.e., the fixed bed gas phase hydrogenation and fluidized bed gas phase hydrogenation according to the different forms of the reactor used. The fixed bed gas phase hydrogenation has the advantages of simple process, low maintenance cost, no need for separation of catalyst, low reaction temperature, good product quality and the like, but local overheating (hot spot) is prone to occur due to poor heat transfer of the fixed bed, which leads to side reactions and deactivation of the catalyst. Therefore, the activity cycle of the catalyst is shortened. For the fluidized bed reactor, heat transfer is good, such that local overheating may be avoided, side reactions may be reduced and the service life of the catalyst may be prolonged. The fluidized bed reactor has the disadvantages of complicated operation, remarkable catalyst abrasion, and high operation and maintenance costs. The liquid phase hydrogenation comprises a gas phase reaction and a liquid phase reaction and achieves easy reaction heat removal, and has the advantages of simple equipment and low operation and maintenance costs, but the cost of technology introduction is high.

Usually, aniline is produced by the liquid phase catalytic hydrogenation process, wherein the raw material nitrobenzene is desulfurized and decarbonized by an oxidation system, the nitrobenzene and hydrogen gas are mixed and pretreated, and then reacted in a fluidized bed reactor and the used catalyst is recycled to the reactor for reuse. Since water is generated in the reaction, the crude product obtained after reaction is refined by extraction, the unreacted nitrobenzene is recovered, aniline is obtained by rectification, and aniline rectification residue is enriched in the rectification tower kettle. The aniline rectification residue is primarily originated from the two aspects: (1) a part of high boiling components is produced from nitrobenzene due to the excess of hydrogen gas in the hydrogenation; (2) cyclohexanone intermediate produced in the hydrogenation reaction may be reacted with aniline to form Schiff base tar, which is black viscous liquid with a pungent smell and contains a lot of aromatic substances with negatively charged π-electron system, such as

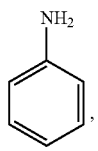

cyclohexyl aniline

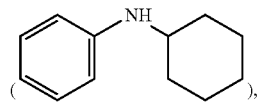

diphenyl amine

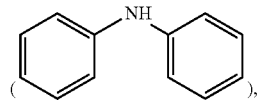

1,2,3,4-tetrahydrocarbazole

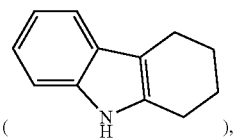 [SMILES: c1ccc2c3c([nH]c2c1)CCCC3]

p-(phenylamino) aniline

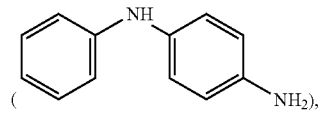

phenol, N-cyclohexyl-1,2-phenylenediamine

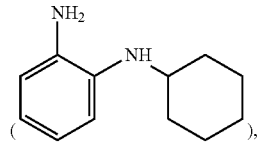

2-phenyl aniline

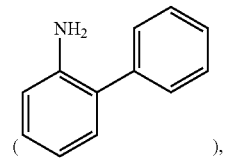 [SMILES: Nc1ccccc1-c1ccccc1]

long chain alkanes and the like. These substances have higher molecular weight, and if the molecules contain an amino group (—NH$_2$), two molecules containing such amino group will take place deamination reaction, so as to form a large molecule containing —NH—. These factors make aniline rectification residue have high viscosity and poor fluidity, and thus difficult to be reused. It is generally used for firewood material and waterproof material. The amount of aniline rectification residue used for the two uses is very small, based on the total amount of aniline rectification residue. Therefore, most of the aniline rectification residue, as waste liquid, is treated by incineration, but after incineration, it will produce nitrogen oxides and lead to acid rain and pollution environment, and further reduce the output of agriculture and fisheries.

The technical problem to be solved by the present invention is how to crack the aniline rectification residue sufficiently to obtain a certain amount of high economic value of product, in order to turn it from waste to treasure and reduce the pollution of the environment as far as possible. At present, there is no effective method for the utilization of aniline rectification residue.

SUMMARY OF THE INVENTION

It is an object of the present invention to provide a catalyst for fixed bed aniline rectification residue recycling, which can hydrocrack aniline rectification residue to break molecular chains C—C, C—N of the high molecular weight substances contained in the residue, to make the C=C molecular chains saturated, to decrease their molecular weight, to reduce the viscosity of the system, to enhance the fluidity, and also to obtain useful substances such as cyclohexyl amine, dicyclohexyl amine and the like such that the subsequent separation operation is facilitated.

Another object of the present invention is to provide a method of preparing the catalyst for fixed bed aniline rectification residue recycling. Said method is simple, and the prepared catalyst has good stability.

A yet another object of the present invention is to provide the use of said catalyst for fixed bed aniline rectification residue recycling.

The technical solution of the present invention used to achieve the above-said object is described as below.

A catalyst for fixed bed aniline rectification residue recycling, which comprises the components described below based on the total weight of the catalyst:
5-40 wt % of NiO as an active component,
2-30 wt % of one or more selected from oxides of Fe, oxides of Mo, oxides of Cr and oxides of Co as a first cocatalyst component,
10-30 wt % of one or more selected from oxides of La, oxides of Zr, oxides of Y and oxides of Ce as a second cocatalyst component,
the remaining portion being the support.

In a preferable embodiment, based on the total weight of the catalyst, it comprises the components described below:
15-30 wt % of NiO as the active component,
5-25 wt % of one or more selected from oxides of Fe, oxides of Mo, oxides of Cr and oxides of Co as the first cocatalyst component,
15-25 wt % of one or more selected from oxides of La, oxides of Zr, oxides of Y and oxides of Ce as the second cocatalyst component,
the remaining portion being the support.

In an embodiment of the catalyst of the present invention, said support is SiO$_2$.

A method of preparing the catalyst for fixed bed aniline rectification residue recycling, which comprises:
A) dissolving nickel nitrate, the nitrates of the metals comprised in the first and second cocatalyst components in water to form the mixing solution of the metal nitrates, and adding dropwise the mixing solution, alkali solution and aqueous sodium silicate solution in a sedimentation tank separately or together in the manner of parallel flow; or
dissolving nickel nitrate, sodium silicate, and the nitrates of the metals comprised in the first and second cocatalyst components in water to form the mixing solution, and adding dropwise the mixing solution and alkali solution in a sedimentation tank separately or together in the manner of parallel flow; or
dissolving nickel nitrate, the nitrates of the metals comprised in the first and second cocatalyst components in water to form the mixing solution of the metal nitrates, and adding dropwise the mixing solution and alkali solution containing dissolved sodium silicate in a sedimentation tank separately or together in the manner of parallel flow; and
B) precipitating the mixture in the sedimentation tank at controlling pH of 7-8, aging, filtering, drying and calcining the resulting precipitate, and then molding and pulverizing it.

When the first cocatalyst component comprises the oxide of Mo, it is different from the above-said method in that the precipitate of the components except Mo is immersed in ammonium molybdate solution, and then calcinated, molded and pulverized.

In an embodiment of the preparation method of the present invention, the concentration of the metal ions in said mixing solution of metal nitrates is controlled at 0.3-5 mol/L.

In an embodiment of the preparation method of the present invention, said alkali solution is aqueous Na$_2$CO$_3$ solution, aqueous NaOH solution or aqueous solution of ammonia, and its concentration is 0.5-10 mol/L.

In an embodiment of the preparation method of the present invention, the concentration of said aqueous sodium silicate solution or the concentration of sodium silicate in alkali solution is 0.1-1 mol/L.

In an embodiment of the preparation method of the present invention, the temperature in the sedimentation tank is controlled at 50-70° C.

In an embodiment of the preparation method of the present invention, the calcination temperature is between 300-700° C., and the calcination time is 4-6 h.

In an embodiment of the preparation method of the present invention, said aging temperature is 60-80° C., and the aging time is 4-8 h; the drying temperature is 100-150° C., and the drying time is 8-15 h.

In an embodiment of the preparation method of the present invention, said molding comprises extrusion molding or compression molding the calcinated catalyst, and the pulverization comprises pulverizing the catalyst to 10-20 mesh.

The present invention additionally provides the use of the above-said catalyst or the catalyst prepared by the above-said method for aniline rectification residue recycling, wherein the aniline rectification residue is treated by gas phase hydrogenation to obtain cyclohexyl amine and dicyclohexyl amine, using monofunctional saturated alcohol as the diluent, under the catalysis of the catalyst, at a certain temperature and pressure.

Said monofunctional saturated alcohol is ethanol or methanol.

The monofunctional saturated alcohol/aniline rectification residue in mass ratio of 0.1-0.7:1 is injected to a fixed bed reactor with the catalyst loading capacity of 10 ml by a micro-metering pump, and is completely evaporated at the upper end of the reaction tube. The liquid phase volume space velocity is 0.6-1.5 h$^{-1}$, the reaction pressure is 1-4 MPa, the reaction temperature is between 250-320° C., the volume ratio of the hydrogen amount and the amount of aniline rectification residue is 500-3000:1, the hydrogen flow rate is 150-400 ml/min. Prior to initiation of the reaction, the catalyst needs to be reduced, and the reduction temperature and time are 350-500° C. and 4 h, respectively. The reducing gas is H$_2$ (50 ml/min). When the reduction is ended and the temperature drops to the reaction temperature, the feeding and reaction is initiated, and the resulting product is quantitatively analyzed by gas chromatograph. The resulting catalyst has high activity and high selectivity, based on the mass of the rectification residue, the cyclohexylamine and dicyclohexylamine yields are up to 36.8% and 40% respectively, and the catalyst has good stability and the product selectivity is still not decreased after 200 h reaction.

The reaction of the aniline rectification residue processed by the catalyst of the present invention belongs to hydrocracking. By hydrocracking, the molecular chains C—C, C—N of the high molecular weight substances contained in the aniline rectification residue are broken, the molecular chains C═C are saturated, the viscosity of the system is decreased, and small molecular substances such as cyclohexyl amine, dicyclohexyl amine are obtained, such that the subsequent separation operation is facilitated. Furthermore, the catalyst of the present invention will not cleave the ring of small molecules, and the reaction principle may refer to the following reaction schemes:

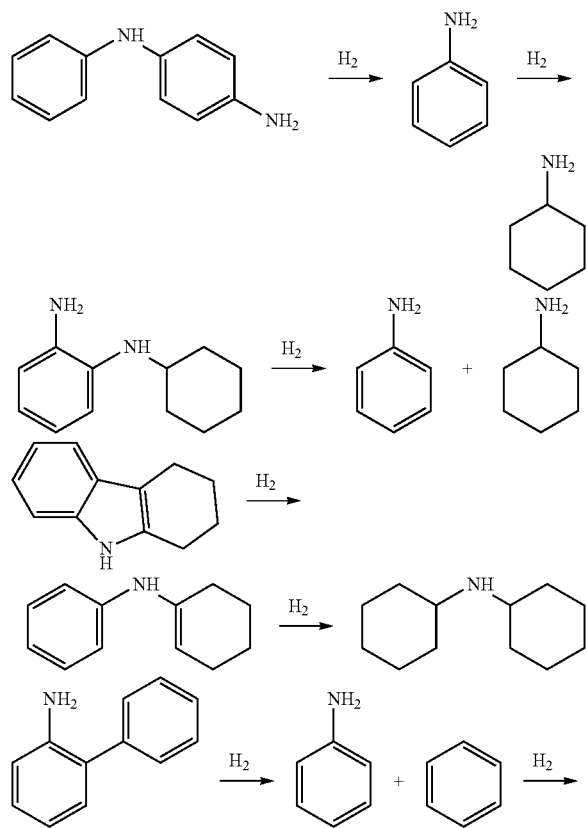

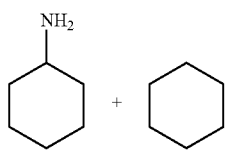

In the catalyst of the present invention, the components have a synergic effect among them, so that the catalyst has high activity and stability. Ni catalyst has good catalytic activity, but is subjected to activity lowering due to the loss, sintering and coking of the active constituents in a high temperature reaction, and prone to sulfur poisoning. By changing the support and adding the first and second cocatalyst components, the loss of the active constituents may be reduced, and the degree of carbon deposition and sintering may be alleviated, thereby enhance the stability of the catalyst and prolong the service life of the catalyst. Y has effects of regulating the catalyst surface acidity, preventing carbon deposition and reducing ring opening reaction. Fe has the role of stabilizing the catalyst, and Mo, Cr, Zr, Ce, La or Co has the functions of reducing carbon deposition on the catalyst and prolonging the life of the catalyst.

BRIEF DESCRIPTION OF THE DRAWINGS

FIG. 1 is the gas chromatogram of the product of Example 1 of the present invention.

THE MODE OF CARRYING OUT THE INVENTION

The embodiments of the present invention are further described with reference to the Examples. The present invention should not be interpreted to be limited to these examples, rather comprise all variations and modifications within the scope of the claims.

The fixed bed reactor used in the Examples have a size of length 100 cm and inner diameter 25 mm. The reaction product is analyzed by Shimadzu GC-2014 gas chromatograph (hydrogen flame ionization (FID) detector) using internal standard method. The detection conditions are as follows: analytical column SE-30, capillary column (Φ0.30 mm×30 m), the gasification chamber 270° C., the detector 270° C. The column temperature is 70° C. and maintained for 1 min, and then rise to 240° C. at the rate of 40° C./min and maintained for 5 min.

The aniline rectification residue used in the Examples is from the aniline rectification units of Ningbo Wanhua Polyurethane Co., Ltd.

Example 1

16 g of nickel nitrate Ni(NO$_3$)$_2$.6H$_2$O, 20 g of ferric nitrate Fe(NO$_3$)$_3$.9H$_2$O and 11 g of lanthanum nitrate La(NO$_3$)$_3$.6H$_2$O are weighed respectively, and dissolved in 300 ml of distilled water, referred to as solution A.

15 mass % of aqueous ammonia solution (200 ml) is formulated, referred to as solution B.

17 g of sodium silicate (Na$_2$SiO$_3$) is weighed and dissolved in 150 ml water, referred to as solution C.

Firstly, 100 ml water in a sedimentation tank is heated to 50° C., and the solution A, B and C are added dropwise to the sedimentation tank. In the preparation process, pH and the precipitation temperature are maintained at 7.5 and 60° C. respectively. After the end of precipitation, the stirring speed and precipitation temperature are kept unchanged, and the resulting precipitate is aged for 4 h, filtered and washed to neutral. Thereafter, the precipitate is placed in an oven of 110° C. and dried for 12 h. After the end of drying, the precipitate is calcined under air atmosphere at 400° C. for 4 h, and then grinded, extrusion molded, pulverized and sieved to 10-20 mesh. Finally, 20% NiO-20% $Fe_2O_3$/40% $SiO_2$-20% $La_2O_3$ is prepared.

10 ml of the above-said catalyst is packed in a fixed bed reactor, and reduced at 400° C. After the reduction, the temperature is lowered to the reaction temperature of 280° C., the system pressure is raised to 1.5 MPa, and the feeding is initiated, wherein the mass ratio of ethanol and aniline rectification residue is 0.2:1. Liquid phase space velocity is 0.7 $h^{-1}$, and $H_2$ flow rate is 200 ml/min. After 10 h reaction, sampling is conducted for analysis, and cyclohexyl amine and dicyclohexyl amine yields are 33.6% and 24%, respectively. After 200 h reaction, cyclohexyl amine and dicyclohexyl amine yields are maintained at 31.2% and 24.6% respectively.

Example 2

24 g of nickel nitrate $Ni(NO_3)_2.6H_2O$, 20 g of ferric nitrate $Fe(NO_3)_3.9H_2O$ and 7 g of yttrium nitrate $Y(NO_3)_3.6H_2O$ are weighed respectively, and dissolved in 300 ml of distilled water, referred to as solution A. 0.7 mol/L of $Na_2CO_3$ solution is formulated, 17 g of sodium silicate ($Na_2SiO_3$) is weighed and dissolved in 300 ml $Na_2CO_3$ solution, referred to as solution B.

Firstly, water in the sedimentation tank is heated to 70° C., and the solution A and B are added dropwise to a sedimentation tank in a parallel flow. In the preparation process, pH and the precipitation temperature are maintained at 8 and 70° C. respectively. After the end of precipitation, the stirring speed and precipitation temperature are kept unchanged, and the resulting precipitate is aged for 4 h, filtered and washed to neutral. Thereafter, the precipitate is placed in an oven of 110° C. and dried for 12 h. After the end of drying, the precipitate is calcined under air atmosphere at 500° C. for 4 h, and then grinded, compression molded, pulverized and sieved to 10-20 mesh. Finally, 30% NiO-20% $Fe_2O_3$/40% $SiO_2$-10% $Y_2O_3$ is prepared.

10 ml of the above-said catalyst is packed in a fixed bed reactor, and reduced at 450° C. After the reduction, the temperature is lowered to the reaction temperature of 300° C., the system pressure is raised to 2 MPa, and the feeding is initiated, wherein the mass ratio of ethanol and aniline rectification residue is 0.2. Liquid phase space velocity is 0.7 $h^{-1}$, and $H_2$ flow rate is 250 ml/min. After 10 h reaction, sampling is conducted for analysis, and cyclohexyl amine and dicyclohexyl amine yields are 36.8% and 40%, respectively. After 200 h reaction, cyclohexyl amine and dicyclohexyl amine yields are maintained at 35.8% and 38.7% respectively.

Example 3

20 g of nickel nitrate $Ni(NO_3)_2.6H_2O$, 8 g of cobalt nitrate $Co(NO_3)_2.6H_2O$ and 15 g of cerium nitrate $Ce(NO_3)_3.6H_2O$ are weighed respectively, and dissolved in 200 ml of distilled water, referred to as solution A.

1 mol/L of NaOH solution is formulated, 17 g of sodium silicate ($Na_2SiO_3$) is dissolved in 200 ml NaOH solution, referred to as solution B.

Firstly, the solution B is poured into a sedimentation tank and heated to 70° C., and the solution A is added dropwise to the sedimentation tank slowly. In the meantime, the precipitation temperature is maintained at 70° C. After the end of precipitation, the stirring speed and precipitation temperature are kept unchanged, and the resulting precipitate is aged for 4 h, filtered and washed to neutral. Thereafter, the precipitate is placed in an oven of 110° C. and dried for 12 h. After the end of drying, the precipitate is calcined under air atmosphere at 550° C. for 4 h, and then grinded, compression molded, pulverized and sieved to 10-20 mesh. Finally, 24% NiO-10% $Co_3O_4$/39% $SiO_2$-27% $CeO_2$ is prepared.

The evaluation of the catalyst is the same as that of Example 2. Cyclohexyl amine and dicyclohexyl amine yields are 31.2% and 33.2%, respectively. After 200 h reaction, cyclohexyl amine and dicyclohexyl amine yields are maintained at 28% and 32.5% respectively.

Example 4

20 g of nickel nitrate $Ni(NO_3)_2.6H_2O$, 17 g of sodium silicate $Na_2SiO_3$, 8 g of cobalt nitrate $Co(NO_3)_2.6H_2O$ and 15 g of cerium nitrate $Ce(NO_3)_3.6H_2O$ are weighed respectively, and dissolved in 200 ml of distilled water, referred to as solution A.

15 mass % of aqueous ammonia solution (200 ml) is formulated, referred to as solution B.

Firstly, the solution A is poured into a sedimentation tank and heated to 70° C., and the solution B is added dropwise to the sedimentation tank slowly. In the meantime, the precipitation temperature is maintained at 70° C. After the end of precipitation, the stirring speed and precipitation temperature are kept unchanged, and the resulting precipitate is aged for 4 h, filtered and washed to neutral. Thereafter, the precipitate is placed in an oven of 110° C. and dried for 12 h. After the end of drying, the precipitate is calcined under air atmosphere at 600° C. for 4 h, and then grinded, compression molded, pulverized and sieved to 10-20 mesh. Finally, 20% NiO-10% $Co_3O_4$/40% $SiO_2$-30% $CeO_2$ is prepared.

The evaluation of the catalyst is the same as that of Example 2. Cyclohexyl amine and dicyclohexyl amine yields are 30.1% and 23.7%, respectively. After 200 h reaction, cyclohexyl amine and dicyclohexyl amine yields are maintained at 28.8% and 22.3% respectively.

Example 5

18 g of nickel nitrate $Ni(NO_3)_2.6H_2O$, 18 g of cobalt nitrate $Co(NO_3)_2.6H_2O$ and 10 g of yttrium nitrate $Y(NO_3)_3.6H_2O$ are weighed respectively, and dissolved in 200 ml of distilled water, referred to as solution A.

200 ml of 1 mol/L of $Na_2CO_3$ solution is formulated, and therein 14.6 g of sodium silicate ($Na_2SiO_3$) is dissolved, referred to as solution B.

Firstly, water in the sedimentation tank is heated to 70° C., and the solution A and B are added dropwise to a sedimentation tank in a parallel flow. In the preparation process, pH and the precipitation temperature are maintained at 8 and 70° C., respectively. After the end of precipitation, the stirring speed and precipitation temperature are kept unchanged, and the resulting precipitate is aged for 4 h, filtered and washed to neutral. Thereafter, the precipitate is placed in an oven of 110° C. and dried for 12 h. After the end of drying, the precipitate is calcined under air atmosphere at 500° C. for 4 h, and then grinded, compression molded, pulverized and sieved to 10-20 mesh. Finally, 24% NiO-25% $Co_3O_4$/36% $SiO_2$-15% $Y_2O_3$ is prepared.

10 ml of the above-said catalyst is packed in a fixed bed reactor, and reduced at 500° C. After the reduction, the temperature is lowered to the reaction temperature of 280° C., the system pressure is raised to 2.5 MPa, and the feeding is initiated, wherein the mass ratio of ethanol and aniline rectification residue is 0.3. Liquid phase space velocity is 0.7 $h^{-1}$, and $H_2$ flow rate is 250 ml/min. After 10 h reaction, sampling is conducted for analysis, and cyclohexyl amine and dicyclohexyl amine yields are 37.2% and 41.5%, respectively. After 200 h reaction, cyclohexyl amine and dicyclohexyl amine yields are maintained at 36.8% and 40.1% respectively.

Example 6

18 g of nickel nitrate $Ni(NO_3)_2.6H_2O$, 18 g of cobalt nitrate $Co(NO_3)_2.6H_2O$, 3 g of zirconium nitrate $Zr(NO_3)_4.5H_2O$, and 5 g of cerium nitrate $Ce(NO_3)_3.6H_2O$ are weighed respectively, and dissolved in 200 ml of distilled water, referred to as solution A.

200 ml of 1 mol/L of $Na_2CO_3$ solution is formulated, and therein 14 g of sodium silicate ($Na_2SiO_3$) is dissolved, referred to as solution B.

Firstly, water in the sedimentation tank is heated to 70° C., and the solution A and B are added dropwise to a sedimentation tank in a parallel flow. In the preparation process, pH and the precipitation temperature are maintained at 8 and 70° C., respectively. After the end of precipitation, the stirring speed and precipitation temperature are kept unchanged, and the resulting precipitate is aged for 4 h, filtered and washed to neutral. Thereafter, the precipitate is placed in an oven of 110° C. and dried for 12 h. After the end of drying, the precipitate is calcined under air atmosphere at 500° C. for 4 h, and then grinded, compression molded, pulverized and sieved to 10-20 mesh. Finally, 24% NiO-25% $Co_3O_4$/36% $SiO_2$-5% $ZrO_2$-10% $CeO_2$ is prepared.

10 ml of the above-said catalyst is packed in a fixed bed reactor, and reduced at 500° C. After the reduction, the temperature is lowered to the reaction temperature of 290° C., the system pressure is raised to 2.5 MPa, and the feeding is initiated, wherein the mass ratio of ethanol and aniline rectification residue is 0.4. Liquid phase space velocity is 0.7 $h^{-1}$, and $H_2$ flow rate is 250 ml/min. After 10 h reaction, sampling is conducted for analysis, and cyclohexyl amine and dicyclohexyl amine yields are 32.5% and 33.7%, respectively. After 200 h reaction, cyclohexyl amine and dicyclohexyl amine yields are maintained at 31.7% and 32.1% respectively.

Example 7

16 g of nickel nitrate $Ni(NO_3)_2.6H_2O$, 11 g of cobalt nitrate $Co(NO_3)_2.6H_2O$, 10 g of ferric nitrate $Fe(NO_3)_3.9H_2O$ and 10 g of yttrium nitrate $Y(NO_3)_3.6H_2O$ are weighed respectively, and dissolved in 200 ml of distilled water, referred to as solution A.

250 ml of 1 mol/L of $Na_2CO_3$ solution is formulated, and therein 16 g of sodium silicate ($Na_2SiO_3$) is dissolved, referred to as solution B.

Firstly, water in the sedimentation tank is heated to 70° C., and the solution A and B are added dropwise to a sedimentation tank in a parallel flow. In the preparation process, pH and the precipitation temperature are maintained at 8 and 70° C., respectively. After the end of precipitation, the stirring speed and precipitation temperature are kept unchanged, and the resulting precipitate is aged for 4 h, filtered and washed to neutral. Thereafter, the precipitate is placed in an oven of 110° C. and dried for 12 h. After the end of drying, the precipitate is calcined under air atmosphere at 500° C. for 5 h, and then grinded, compression molded, pulverized and sieved to 10-20 mesh. Finally, 20% NiO-15% $Co_3O_4$-10% $Fe_2O_3$/40% $SiO_2$-15% $Y_2O_3$ is prepared.

10 ml of the above-said catalyst is packed in a fixed bed reactor, and reduced at 500° C. After the reduction, the temperature is lowered to the reaction temperature of 300° C., the system pressure is raised to 2.5 MPa, and the feeding is initiated, wherein the mass ratio of ethanol and aniline rectification residue is 0.4. Liquid phase space velocity is 0.7 $h^{-1}$, and $H_2$ flow rate is 250 ml/min. After 10 h reaction, sampling is conducted for analysis, and cyclohexyl amine and dicyclohexyl amine yields are 36.9% and 40.2%, respectively. After 200 h reaction, cyclohexyl amine and dicyclohexyl amine yields are maintained at 35.8% and 39.5% respectively.

Example 8

24 g of nickel nitrate $Ni(NO_3)_2.6H_2O$ and 14 g of yttrium nitrate $Y(NO_3)_3.6H_2O$ are weighed respectively, and dissolved in 300 ml of distilled water, referred to as solution A. 300 ml of 0.7 mol/L of $Na_2CO_3$ solution is formulated, and 17 g of sodium silicate ($Na_2SiO_3$) is weighed and dissolved in the $Na_2CO_3$ solution, referred to as solution B.

Firstly, water in the sedimentation tank is heated to 70° C., and the solution A and B are added dropwise to a sedimentation tank in a parallel flow. In the preparation process, pH and the precipitation temperature are maintained at 8 and 70° C., respectively. After the end of precipitation, the stirring speed and precipitation temperature are kept unchanged, and the resulting precipitate is aged for 4 h, filtered and washed to neutral. Thereafter, the precipitate is placed in an oven of 110° C. and dried for 12 h. After the end of drying, the resulting catalyst is immersed in ammonium molybdate $((NH_4)_6Mo_7O_{24}.4H_2O)$ solution for 5 h, calcined under air atmosphere at 500° C. for 4 h, and then grinded, compression molded, pulverized and sieved to 10-20 mesh. Finally, 30% NiO-10% $MoO_3$/40% $SiO_2$-20% $Y_2O_3$ is prepared.

10 ml of the above-said catalyst is packed in a fixed bed reactor, and reduced at 450° C. After the reduction, the temperature is lowered to the reaction temperature of 300° C., the system pressure is raised to 2 MPa, and the feeding is initiated, wherein the mass ratio of ethanol and aniline rectification residue is 0.2. Liquid phase space velocity is 0.7 $h^{-1}$, and $H_2$ flow rate is 250 ml/min. After 10 h reaction, sampling is conducted for analysis, and cyclohexyl amine and dicyclohexyl amine yields are 38.8% and 36.7%, respectively. After 200 h reaction, cyclohexyl amine and dicyclohexyl amine yields are maintained at 36.2% and 34.5% respectively.

Example 9

20 g of nickel nitrate $Ni(NO_3)_2.6H_2O$, 17 g of sodium silicate $Na_2SiO_3$, 8 g of chromium nitrate $Cr(NO_3)_3.9H_2O$ and 15 g of cerium nitrate $Ce(NO_3)_3.6H_2O$ are weighed respectively, and dissolved in 200 ml of distilled water, referred to as solution A.

20 mass % of aqueous ammonia solution (150 ml) is formulated, referred to as solution B.

Firstly, the solution A is poured into a sedimentation tank and heated to 70° C., and the solution B is added dropwise to the sedimentation tank slowly. In the meantime, the precipitation temperature is maintained at 70° C. After the end of precipitation, the stirring speed and precipitation temperature are kept unchanged, and the resulting precipitate is aged for 4 h, filtered and washed to neutral. Thereafter, the precipitate is placed in an oven of 110° C. and dried for 12 h. After the end of drying, the precipitate is calcined under air atmosphere at 600° C. for 3 h, and then grinded, compression molded, pulverized and sieved to 10-20 mesh. Finally, 24.5% NiO-7.2% $Cr_2O_3$/39.9% $SiO_2$-28.4% $CeO_2$ is prepared.

The evaluation of the catalyst is the same as that of Example 2. Cyclohexyl amine and dicyclohexyl amine yields are 28.3% and 20.7%, respectively. After 200 h reaction, cyclohexyl amine and dicyclohexyl amine yields are maintained at 25.8% and 18.4% respectively.

What is claimed is:

1. A process of recycling aniline rectification residue, comprising subjecting the aniline rectification residue to fixed bed hydrogenation with a catalyst, wherein said catalyst comprises the components described below based on the total weight of the catalyst:
   5-40 wt % of NiO as an active component,
   2-30 wt % of one or more selected from oxides of Fe, oxides of Mo, oxides of Cr and oxides of Co as a first cocatalyst component,
   10-30 wt % of one or more selected from oxides of La, oxides of Zr, oxides of Y and oxides of Ce as a second cocatalyst component,
   the remaining portion being the support.

2. The process of claim 1, wherein said catalyst comprises the components described below based on the total weight of the catalyst:
   15-30 wt % of NiO as the active component,
   5-25 wt % of one or more selected from oxides of Fe, oxides of Mo, oxides of Cr and oxides of Co as the first cocatalyst component,
   15-25 wt % of one or more selected from oxides of La, oxides of Zr, oxides of Y and oxides of Ce as the second cocatalyst component,
   the remaining portion being the support.

3. The process of claim 1, wherein the support is $SiO_2$.

4. The process of claim 1, wherein the aniline rectification residue is treated by gas phase hydrogenation to obtain cyclohexyl amine and dicyclohexyl amine, using monofunctional saturated alcohol as the diluent, under the catalysis of the catalyst, at a certain temperature and pressure.

5. The process of claim 4, wherein the monofunctional saturated alcohol is ethanol or methanol.

6. The process of claim 4, wherein the monofunctional saturated alcohol/aniline rectification residue in mass ratio of 0.1-0.7:1 is introduced to a fixed bed reactor, wherein the liquid phase volume space velocity is 0.6-1.5 $h^{-1}$, the reaction pressure is 1-4 MPa, the reaction temperature is between 250-320° C., and the volume ratio of the hydrogen amount and the amount of aniline rectification residue is 500-3000:1.

* * * * *